United States Patent
Flinsenberg et al.

(10) Patent No.: US 9,652,960 B2
(45) Date of Patent: May 16, 2017

(54) DEVICE AND METHOD FOR ROUTING A MEDICAL ALERT TO A SELECTED STAFF MEMBER

(71) Applicant: KONINKLIJKE PHILIPS N.V., Eindhoven (NL)

(72) Inventors: Ingrid Christina Maria Flinsenberg, Eindhoven (NL); Roel Peter Geert Cuppen, Venlo (NL); Rosemarie Jolanda Elise Rajae-Joordens, Asten (NL); Elke Marieke Lambert Daemen, Meerhout (BE); Evert Jan Van Loenen, Waalre (NL)

(73) Assignee: Koninklijke Philips N.V., Eindhoven (NL)

( * ) Notice: Subject to any disclaimer, the term of this patent is extended or adjusted under 35 U.S.C. 154(b) by 40 days.

(21) Appl. No.: 14/396,985

(22) PCT Filed: Apr. 15, 2013

(86) PCT No.: PCT/IB2013/052984
§ 371 (c)(1),
(2) Date: Oct. 24, 2014

(87) PCT Pub. No.: WO2013/164721
PCT Pub. Date: Nov. 7, 2013

(65) Prior Publication Data
US 2015/0116112 A1    Apr. 30, 2015

Related U.S. Application Data

(60) Provisional application No. 61/641,337, filed on May 2, 2012.

(51) Int. Cl.
G08B 1/08    (2006.01)
G08B 21/02    (2006.01)
(Continued)

(52) U.S. Cl.
CPC .......... *G08B 21/02* (2013.01); *G06F 19/327* (2013.01); *G06F 19/3418* (2013.01); *G08B 25/016* (2013.01)

(58) Field of Classification Search
None
See application file for complete search history.

(56) References Cited

U.S. PATENT DOCUMENTS 5,534,851 A    7/1996 Russek
5,594,786 A    1/1997 Chaco et al.
(Continued)

FOREIGN PATENT DOCUMENTS

CN    102110347 A    6/2011
WO    9503596 A2    2/1995
WO    2007081823 A2    7/2007

*Primary Examiner* — Nabil Syed
*Assistant Examiner* — Thomas McCormack (57) ABSTRACT

A method for routing a medical alert to a selected staff member 151-153, the method comprising receiving an alert signal generated by an alert generation device 121-126, obtaining the current location and identity of multiple staff members from a location tracking system 141-146 configured to track the locations of the multiple staff members, upon receiving the alert signal, selecting from the multiple staff members a selected staff member by at least determining that the distance between a location of the alert generation device and the location of the selected staff member is shorter than the distance between the location of the alert generation device and the location of at least one of the multiple staff members other than the selected staff member, and sending an alert signal to an individually addressable mobile device associated with the selected staff member.

15 Claims, 3 Drawing Sheets

(51) Int. Cl.
    *G06F 19/00*     (2011.01)
    *G08B 25/01*     (2006.01)

(56) References Cited

U.S. PATENT DOCUMENTS

| | | | |
|---|---|---|---|
| 2005/0242928 A1* | 11/2005 | Kirkeby | G08B 5/22 340/286.07 |
| 2008/0018436 A1 | 1/2008 | Traughber et al. | |
| 2009/0046837 A1* | 2/2009 | Thiel | H04M 11/04 379/37 |
| 2009/0058635 A1* | 3/2009 | LaLonde | A61N 1/37282 340/539.11 |
| 2012/0314901 A1* | 12/2012 | Hanson | A61B 5/1117 382/103 |

* cited by examiner

DEVICE AND METHOD FOR ROUTING A MEDICAL ALERT TO A SELECTED STAFF MEMBER

CROSS-REFERENCE TO PRIOR APPLICATIONS

This application is the U.S. National Phase application under 35 U.S.C. §371 of International Application No. PCT/IB2013/052984, filed on Apr. 15, 2013, which claims the benefit of U.S. Provisional Application No. 61/641,337, filed on May 2, 2012. This application is hereby incorporated by reference herein.

FIELD OF THE INVENTION

The invention relates to a method for routing a medical alert to a selected staff member, the method comprising receiving an alert signal generated by an alert generation device, and sending an alert signal to a staff member.

The invention further relates to corresponding software and an alert router.

BACKGROUND OF THE INVENTION

U.S. Pat. No. 5,534,851 discloses a known alarm system for notifying necessary medical and hospital personnel that a patient or the patient's life support equipment require immediate response without providing the alarm signal to the monitored patient or surrounding patients.

An alarm signal pulse generator takes the status output signal from a medical equipment monitor sensor and converts that signal into a coded pulse that identifies the patient, the room, the ambulance or other relevant location information. The output of the alarm signal pulse generator is communicated to a master alarm control. The master control includes an antenna to simultaneously transmit a signal to an appropriate group of pagers.

Using a keyboard a user inputs the names of hospital staff assigned to each patient, to each room, and to each type of medical condition as well as the availability of those individuals to respond to emergency calls.

The master alarm control transmits an RF signal to a plurality of pagers. The transmitted signals from the master control unit may be coded in such a way that only particular pagers held by certain personnel would be activated, e.g., the technicians that deal strictly with ventilators may have a certain code that would not disturb other personnel within a given area.

SUMMARY OF THE INVENTION

It would be advantageous to have an improved a method for routing a medical alert. For example, the known alarm system routes an alarm to a group of pagers. This has the effect that either too many or too few of the paged individuals respond. Furthermore, assignment or availability date is always out of date since they are inputted using a keyboard.

A method for routing a medical alert to a selected staff member is provided. The method comprises receiving an alert signal generated by an alert generation device, obtaining the current location and identity of multiple staff members from a location tracking system configured to track the locations of the multiple staff members, upon receiving the alert signal, selecting from the multiple staff members a selected staff member by at least determining that the distance between a location of the alert generation device and the location of the selected staff member is shorter than the distance between the location of the alert generation device and the location of at least one of the multiple staff members other than the selected staff member, and sending an alert signal to an individually addressable mobile device associated with the selected staff member.

The method improves the routing of medical alerts. When an alert generation device generates an alert signal, say in response to a sensor reaching a critical value a selected staff member is selected from multiple staff members. An alarm signal is then sent to an individually addressable mobile device associated with the selected staff member. Since the mobile device is individually addressable, there is no need for staff members that are not required to respond to the alert signal to receive an alert signal. Moreover, since the location of staff members is tracked it is possible to select a staff member that is close to the origin of the alert, i.e., closer than some other staff member. These two factors combine to reduce response time. The selected staff member is individually addressed thus making it clear that a response is required, furthermore, that staff member is closer to the alert origin than another staff member would be, so the time needed to go to the origin of the alert is reduced.

The inventors have observed that during the stay at a hospital alerts play an important role. The alerts, such as alarms of monitoring equipment, nurse calls, etc, may have a negative impact on the healing process, especially, when they cause noise. The invention reduces this negative impact by reducing the response time to the alert. At the same time flexibility is increased; staff members need not be assigned to particular rooms since their location is tracked by a location tracking system.

A medical alert may be triggered, i.e. generated upon, various events. An alert generation device may comprise a button for a patient to press manually; upon pressing the button the alert signal is generated. The alert signal may be triggered by monitoring equipment. An alert may be given if a sensor reading exceeds above or drops below an alert value. The alert signal may be accompanied by an alarm which may cause (a lot) of noise. Other alerts are possible. In an embodiment, the alert signal comprises an alert type, e.g., the type of equipment the generated the alert, or the particular alert value that was passed, etc. The alert may also include an alert location, i.e., the current location of the alarm generating device at the time of the alert.

Particularly interesting are alert generation devices that are mobile, for example configured to be carried with a patient. The use of mobile alert generation devices makes tracking the location of staff members even more advantageous. It is unknown in advance which staff member will be in the neighborhood of which alert generation devices. Mobile alert generation devices allow a patient more mobility without compromising on safety. An embodiment comprises obtaining the current location of the mobile alert generation device from a location tracking system configured to track the locations of the mobile alert generation device. The location tracking system configured to track the locations of the mobile alert generation device may be the same as the location tracking system configured to track the locations of the multiple staff members.

For example, an embodiment comprises detecting that the location of the mobile alert generation device remains in an alert area for a period exceeding an alert period. The alert area is a geographical area, which is typically predetermined. For example, the alert area may be the bathroom. If a patient stays in the bathroom too long it may indicate an accident. The detecting may be done by a detection device configured to detect that the mobile alert generation device enters the alert area, tracking the mobile alert device until the mobile alert device leaves the alert area or the alert period passed since the moment entering detection; in the latter case, upon passing of the alert period the detection device generates an alert, e.g., comprising a 'too long in alert area' alert type.

Other conditions which may generate an alert include: detecting that a patient lays on one side too long, detecting that an mobile alert generating device leaves a particular area, or leaves during certain periods, e.g., leaving the ward, getting out of bed at night, getting out of bed at the wrong side of the bed, leaving a bedroom at night, etc.

Automatically detecting fall accidents may be done with fall detectors based, e.g., on a combination of accelerometers and pressure sensors. In case a person falls who is wearing the fall detector an alert is generated. In an embodiment, the mobile alert generation device comprises a fall detector, the mobile alert generation device being configured to generate the alert upon the fall detector detecting the fall of a person carrying the mobile alert generation device.

A staff member may be a medically trained staff member, e.g., a nurse or a doctor. But a staff member may also be untrained, e.g., volunteers. A staff member may be trained for specific tasks, e.g., maintenance to specific devices such as monitoring devices.

The location tracking system for determining the locations of staff members or for the determining of the location of a mobile alert generating device may detect the room or area in which the staff members reside or the room or area from which the alert originates. Often this level of precision is sufficient. Furthermore, location tracking system determines the identity of each staff member and possibly that of the patient. This identity could be a unique identity, e.g., a name or unique identifier, or a non-unique identity such as the staff member's role, such as nurse, head nurse, doctor, therapist, etc. Many different localization systems may be used, e.g., an RF-ID based system, IR-RF based system, video, or audio system. Localization of staff members may use a different system, say a video based system, so that staff members need not carry a special ID tag, whereas the localization of the origin of the alert may be integrated with the alert generating device. They may use the same system. The individually addressable mobile device may also be used to track its associated staff member. Typically, the localization system comprises multiple localization receivers distributed over multiple rooms and multiple location tags, each staff member carrying a location tag, the locations tag cooperating with the localization receivers so that the localization receivers track the location of the multiple location tags, for example, the room a tag is currently in. For example, the individually addressable mobile device may be configured for WLAN communications, say WiFi; a series of WiFi receivers may keep track of the location of the device.

The alert signal may be received by a central system, say, an alert router. Selecting from the multiple staff members typically involves three components, determine who is suitable to respond to the alert signal, determining who is available to respond to the alert signal, and determining who is close to the origin of the alert signal. A combination that has worked well is to select the staff member who is suitable and available and nearest to the origin of the alert signal. It is not strictly necessary to select the absolute closest. Other considerations may determine who is selected, e.g., a better distribution of work, etc.

The system may use as input the locations of all staff members and the location of the incoming alert to determine the nearest staff member(s) upon the generation of an alert. Given the available suitable staff members, the system may determine the nearest one to the alert. In an embodiment, a particular staff member is determined as suitable if suitability criteria associated with the identity of a staff member match the alert type.

Determining suitable staff member(s) upon the generation of an alert may include determining the identity of each staff member and that of the patient. For example, based on the type of alert, the system determines which of the available staff members are suitable to react to the alert. For example, a therapist may not be suited to respond to a nurse call. If none of the present staff members are suited to respond to the alert, e.g., in case of emergencies, the method may ignore the suitability criteria and continue by considering all staff members that are present.

Availability to respond to an alert may depend on the current activities of the staff members. In one system, all staff members are initially marked as available and marked off as unavailable following certain conditions. In an embodiment, a staff member is determined as unavailable if its location is in a defined unavailability area. For example, if the location of a staff member is in a particular area, such as a patient bath room, he is probably busy, say washing the patient. Other sensing modalities can be used as well to determine the current staff activities. Alternatively, this step in the procedure can be left out, e.g., in case of emergencies, say, if none of the suitable staff members are available, the system ignores the availability criterion and continues with all suitable staff members.

Individually addressable mobile devices are capable of receiving a message addressed only to that particular device. An individually addressable mobile device may be a mobile phone. Also a PDA or a tablet PC and the like may be configured as an individually addressable mobile device. For example, the alerts are sent to a mobile device carried by the staff members. Individually addressable mobile device may be associated with a staff member, e.g., with the identity of the staff member, through a database.

After the selected staff member received the alert signal sent to his mobile device, the selected staff member may send a response message. For example, the method may include receiving from the selected staff member an expected response time. The staff member may give the respond message with his mobile device.

In an embodiment, the patient is informed that a selected staff member has received an alert signal. Preferably, the patient is also informed when the selected staff member will follow-up with the alert. In an embodiment, the patient is informed on a display. For example, a message is displayed on a display that comprises the expected response time. An embodiment comprises selecting from multiple displays a selected display closest to the location of the alert generation device, in particular, closest to the location of the mobile alert generation device. Alternatively, the one may select from multiple displays a selected display closest to the location of the alert generation device and in the same room as the alert generation device. At least, one selects a display out of the multiple displays that is closer to the alert generation device than at least one display of the multiple displays other than the selected display. Sending a message to the selected display for display is done after receiving the alert signal and typically after sending an alert to the selected staff member.

Preferably, a patient is informed when a staff member indicates he will follow-up with the alert. For example, a staff member that receives an alert may be required to respond to that message and indicate his responsiveness. For example, whether he can respond to the alert, e.g., now, later, say in 5 minutes, or not at all. Based on this response the messages can be updated. If the selected staff member does not respond to the alert message within a certain time interval, the alert may be sent to the next nearest suitable available staff member. If the staff member does respond but the indicated responsiveness is too slow, the alert may also be sent to the next nearest available suitable staff member. The system may also check the follow-up of the indicated responsiveness so that if the difference between the indicated responsiveness and the actual situation becomes too large, the system re-sends the alert to the staff member and/or send the alert to the next nearest suitable available staff member. The response of the selected staff member may be used to inform the patient that the alert has been received and/or how long it may take for a staff member to respond. The messages to the patients may be sent to a display, say near to the patient. In particular, the system may determine the nearest display, e.g., by comparing the location of the origin of the alert generation device, say a current location determined for a mobile alert generation device, and compare it to a list of stationary devices, say as arranged in a database, and select the nearest one or select the nearest one in the same room. For the latter purpose the database may contain a representation of the range of locations in the room in which a display is located. The database may specify the nearest visible display for each location.

The system may also inform the selected staff member(s) about any one of: the type of the alert, the name and location of the patient, and other information. When a suitable staff member meets the patient, the alert may be considered solved and all outstanding messages regarding this alert are removed from the system. The system may be arranged for staff members to check if there are alerts outstanding for which they are suitable responders.

In an embodiment, the method comprises determining that only one staff member is available and/or suitable, selecting said staff member and sending an alert signal to an individually addressable mobile device associated with the selected staff member. For example, given two available staff members of which only the staff member who is furthest from the alert origin is suitable, the method may select the only suitable and available staff member.

An aspect of the invention concerns an alert router for routing a medical alert to a selected staff member, the alert router comprising a receiver configured to receive an alert signal generated by an alert generation device, a location obtainer configured to obtain the current location and identity of multiple staff members from a location tracking system configured to track the locations of the multiple staff members, a selector configured to upon receiving the alert signal, selecting from the multiple staff members a selected staff member by at least determining that the distance between a location of the alert generation device and the location of the selected staff member is shorter than the distance between the location of the alert generation device and the location of at least one of the multiple staff members other than the selected staff member, an alert signal sender configured to send an alert signal to an individually addressable mobile device associated with the selected staff member.

An aspect of the invention concerns a system for routing a medical alert to a selected staff member. The system comprises a an alert router for routing a medical alert to a selected staff member, a location tracking system configured to track the locations of the multiple staff members and optionally multiple individually addressable mobile device each associated with one of the multiple staff members The router and individually addressable mobile device may be implemented using an electronic device, in particular a computer.

A method according to the invention may be implemented on a computer as a computer implemented method, or in dedicated hardware, or in a combination of both. Executable code for a method according to the invention may be stored on a computer program product. Examples of computer program products include memory devices, optical storage devices, integrated circuits, servers, online software, etc. Preferably, the computer program product comprises non-transitory program code means stored on a computer readable medium for performing a method according to the invention when said program product is executed on a computer In a preferred embodiment, the computer program comprises computer program code means adapted to perform all the steps of a method according to the invention when the computer program is run on a computer. Preferably, the computer program is embodied on a computer readable medium.

BRIEF DESCRIPTION OF THE DRAWINGS

These and other aspects of the invention are apparent from and will be elucidated with reference to the embodiments described hereinafter. In the drawings.

It should be noted that items which have the same reference numbers in different Figures, have the same structural features and the same functions, or are the same signals. Where the function and/or structure of such an item has been explained, there is no necessity for repeated explanation thereof in the detailed description.

LIST OF REFERENCE NUMERALS 100 a hospital ward
101-107 rooms
121-126 alert generation devices
131-134 displays
141-146 localization devices
151-153 staff members
160 an alert router
310 a receiver configured to receive an alert signal
312 a suitability determiner
314 a suitability database
320 a location obtainer
322 an availability determiner
324 an unavailability area database
330 a selector
340 an alert signal sender
350 a display sender
352 a display location database
354 an expected response time receiver
400 a method for routing a medical alert to a selected staff member
410 receiving an alert signal 420 obtaining the current location and identity of multiple staff members
430 selecting a selected staff member
440 sending an alert signal to the selected staff member

DETAILED EMBODIMENTS

While this invention is susceptible of embodiment in many different forms, there is shown in the drawings and will herein be described in detail one or more specific embodiments, with the understanding that the present disclosure is to be considered as exemplary of the principles of the invention and not intended to limit the invention to the specific embodiments shown and described.

Figure 1:
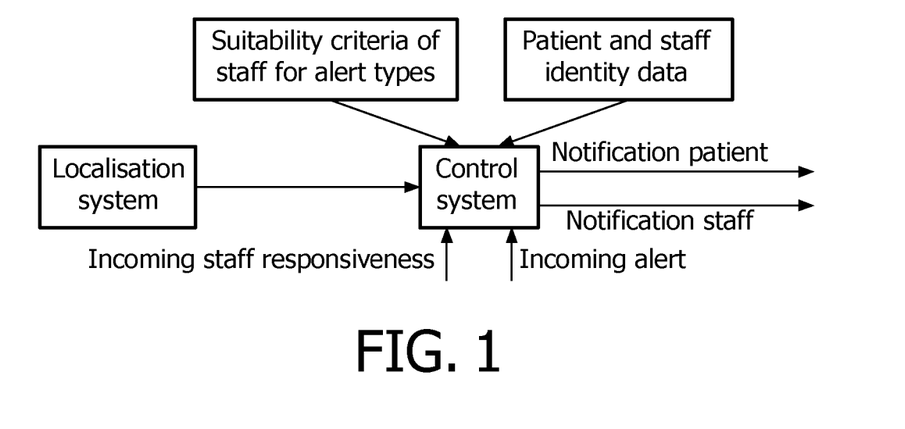
FIG. 1 is a block diagram illustrating alert routing.

FIG. 1 is a block diagram illustrating an alert routing system. Shown is a control system that receives information from various sources. Through a localization system the control system receives the current location and identity of multiple staff members. An incoming alert is received from an alert generating device. Suitability criteria of staff for the alert types are obtained by the control system. By applying the suitability criteria to the alert type the control system determines which staff members are suitable. If needed, also availability data may be obtained to determine which staff members are available. The control system may select a staff member that is suitable according to the criteria and is near the origin of the alert, for example, nearest. The control system sends an alert to the selected staff member, using a mobile device associated with the selected staff member. From the selected staff member responsiveness data may be obtained. The patient is sent a notification, e.g., based on the responsiveness data. Other staff, i.e., non-selected staff members may be sent a notification so that they know an alert is ongoing and that another staff member was selected to respond to the alert.

Figure 2:
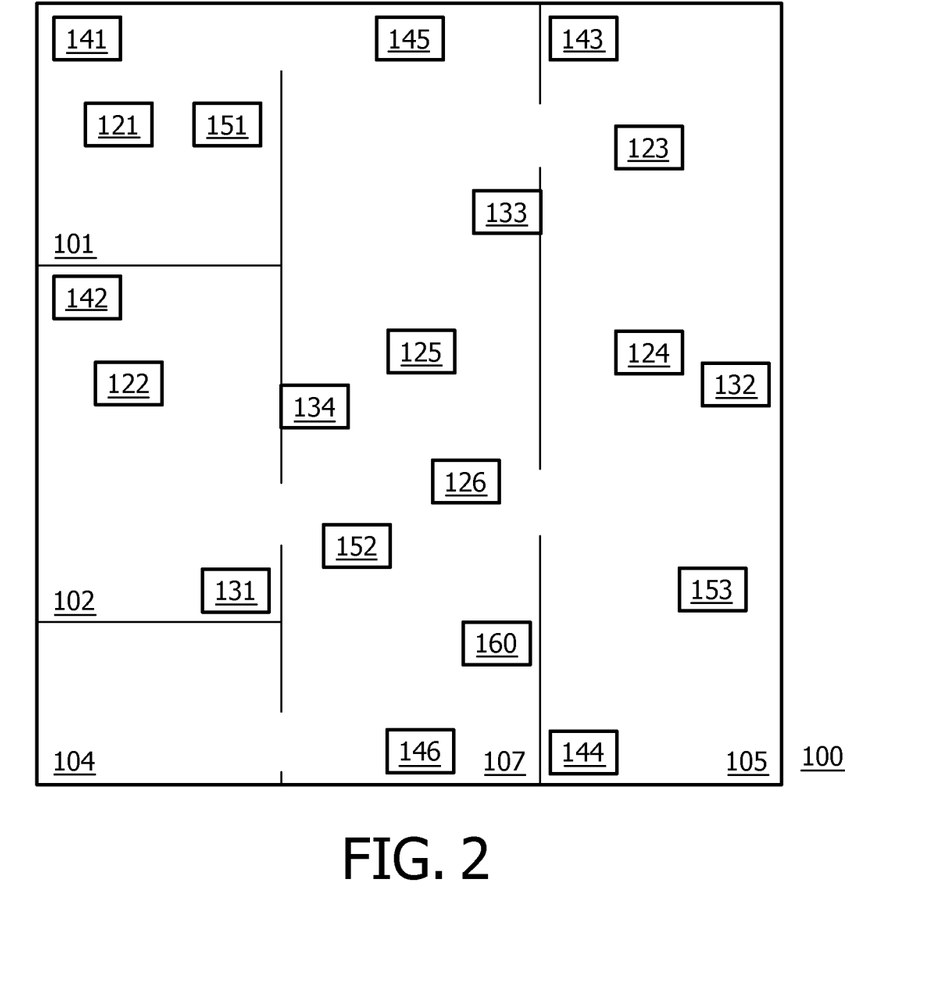
FIG. 2 is schematic map of a ward.

FIG. 2 is schematic map of a ward, say a hospital ward. The invention is also applicable to a variety of alert situations, e.g., prisons, retirement homes, sheltered housing, assisted living, and the like.

FIG. 2 shows rooms 101, 102, 104, 105 and 107. Room 107 is a central hallway. The number of rooms, their arrangement and relative sizes has been chosen to illustrate the invention and are not limiting. Distributed across ward 100 are several alert generation devices. Typically, each alert generation device is carried by, connected to, or in the vicinity of a person, e.g., a patient. Shown are devices 121, 122, 123, 124, 125 and 126. Distributed across ward 100 are multiple staff members; three staff members are shown: staff member 151, 152 and 153, Each staff member carries an individually addressable mobile device (not separately shown).

The ward has a location tracking system configured to track the locations of the multiple staff members. In this particular ward, the location tracking system comprises multiple location tracking devices, distributed across the ward, each configured to detect the presence of a staff member in a particular area. Shown are location tracking devices 141, 142, 143, 144, 145, and 146. Each one of the multiple staff member carries a location tracking beacon configured to be detected by the location tracking devices. The location tracking devices may be combined with the individually addressable mobile device also carried by the staff member.

Some alert generation devices are mobile. In ward 100, devices 125 and 126 are mobile and are carried by a person. For example, alert generation devices 125 and 126 may be fall detectors. The location of alert generation devices may also be trackable, preferably, at least the mobile alert generation devices are trackable. The location tracking system may also track the location of the alert generation devices. Alert generation devices and staff members may carry a beacon, say an RFID tag, to make their location trackable.

Across the ward multiple displays are distributed. Shown are displays 131, 132, 133 and 134. Finally an alert router 160 is shown. Alert router 160 need not necessarily be located on ward 100, or even near ward 100. However, alert router 160 is configured to receive information from the alert generation devices and localization devices, and is able to send messages to the displays and to the mobile devices of the staff. For example, router 160 may be connected via a network, possibly a wireless network, say WLAN.

Figure 3:
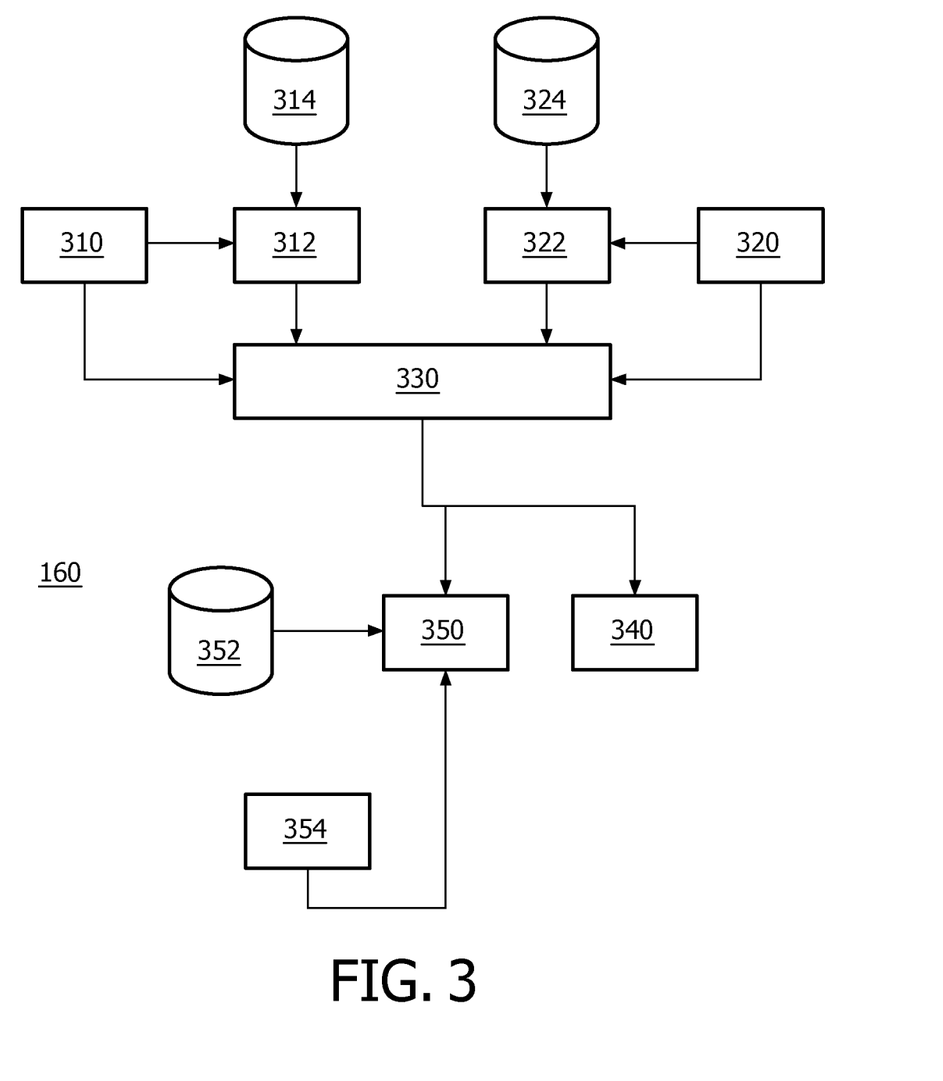
FIG. 3 is a block diagram of a system of an alert router.
Figure 4:
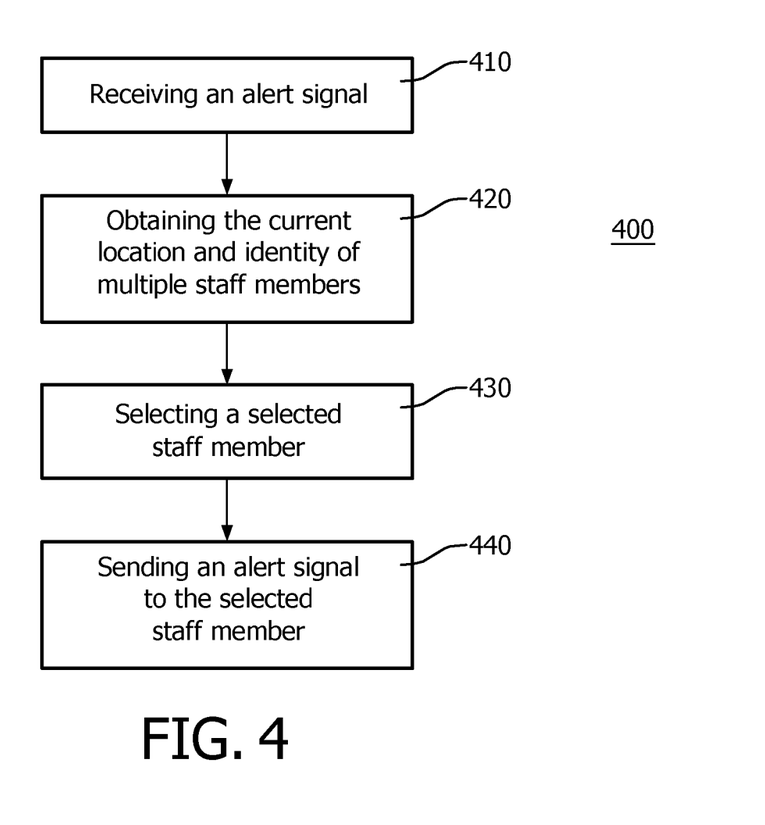
FIG. 4 is schematic flow chart of a method for alert routing.

FIG. 3 is a block diagram of alert router 160. The invention may be embodied using a centralized alert router, like the one shown in FIG. 3. However, the functionality of the alert router could be distributed across multiple devices, say, across, the individually addressable mobile devices, alert generation devices and/or locatable devices. FIG. 4 illustrates in a schematic flow chart a method for alert routing, which may be used by the alert router of FIG. 3, or more generally by a system as shown in FIG. 1.

Alert router 160 comprises a receiver 310 configured to receive an alert signal, e.g. from any one of multiple alert generation devices, say devices 121-126. Alert router 160 comprises a location obtainer 320 configured to obtain the current location and identity of multiple staff members from a location tracking system configured to track the locations of the multiple staff members. For example obtainer 320 may obtain the location of staff members 151-153, e.g., through devices 141-146. Both the alert receiver 310 as the location obtainer 329 may comprise a network port or antenna to receive their data through wired or wireless connection respectively.

Router 160 is also configured to obtain the location of the origin of an alert. If the ward does not use mobile alert generation devices, it is sufficient for an alert generation device to identify itself, say through a unique number, its location may then be looked up, e.g., in a database. The location of an alert generation device may be comprised in an alert generated by it. In the latter case the location is received through receiver 310. The location may also be determined using the location tracking system. In the latter case the location is obtained through obtainer 320.

Router 160 comprises a selector 330 for selecting from the multiple staff members, say 151-153, a selected staff member. Many issues may be considered by selector 330 but at least it determines that the selected staff member is closer to other staff members. Embodiments may be simplified, by having selector 330 simplify selects the staff member whose location is nearest to the origin of an alert, possibly taking other criteria into account such as suitability and availability.

Router 160 comprises an alert signal sender 340 for sending an alert signal to an individually addressable mobile device associated with the selected staff member.

Router 160 may use method 400 of the flowchart in FIG. 4. For example, suppose that an alert generation device generates an alert, say alert generation device 124 in room 105. The alert is passed, say, wirelessly, to router 160. Router 160 receives 410 the alert signal. Router 160 obtains 420 the current location and identity of multiple staff members. For example, router 160 determines that staff member 151 is in room 101, staff member 152 is in room 107 and staff member 153 in room 105. Router 160 then selects 430 staff member 153, which is closer to the origin of the alert, than the other staff members. For example router 160 has selected a staff member, as being the closest. Router 160 then sends a signal 440 to a mobile device of selected staff member 153.

In a more refined embodiment, the router 160 may further comprises a suitability determiner 312 and a suitability database 314. The alert that is received through receiver 310 comprises an alert type, say a fall, a device malfunction, a heart failure, etc. Database 314 comprises suitability criteria. For example, for a fall any medically schooled staff member is suitable. For a device malfunction only a technically schooled staff member might be suitable. Before selecting a staff member, selector 330 first filters out those staff members that are suitable. The alert type may be implemented as bit string having a length, a particular place in the bit string indicating a particular alert type. A suitability criterion may be a bit string having the same length as the alert type. A particular place in the suitability bit string indicating suitability for the particular alert type. Database 314 may store a suitability bit string for all staff members of the multiple staff members. A non zero result after an 'AND' operation may indicate suitability.

In a more refined embodiment, the router 160 may further comprise an availability determiner 322 and an unavailability area database 324. The availability determiner 322 is configured to determine if a staff member is available. For example, availability determiner 322 receives the location of all staff members. All staff members whose location is in a defined unavailability area, say as listed in database 324, are marked as available. For example, room 101 may be a bathroom. Staff member 151 is tracked as present in that room by device 141. Room 101 is a defined unavailability area in database 324. Availability determiner 322 determines that staff member 151 is likely busy, and will mark him/her as unavailable. Staff members 152 and 153 are not marked as unavailable and thus as available. Availability determiner 322 may use other criteria to determine availability, possibly in combination, for example, a staff member that received an alert less than some particular time ago, is likely busy responding to the previous alert and thus unavailable.

Selector 330 receives from a suitability determiner 312 and availability determiner 322 which staff members are suitable and available. Selector 330 may combine this information to obtain staff members that are both suitable and available. Alternatively, availability determiner 322 may receive input from suitability determiner 312 and only determine availability for suitable staff members (or the other way round).

Selector 330 may determine which staff member of the suitable and available staff members are near the origin of the alert. Selector 330 may select the nearest suitable and available staff member. But selector 330 may also involve other criteria. For example, the system may strive to keep the amount of work for each staff member approximately equal.

Router 160 comprises an alert signal sender 340 for sending an alert to the selected staff member. Alert signal sender 340 is configured to look-up the associated mobile device associated with the selected staff member and then sends the alert to him at the mobile device. Alert signal sender 340 will typically send the alert wirelessly through an antenna. For example, alert signal sender 340 may send an SMS message.

Router 160 may comprise an expected response time receiver 354 for receiving from the selected staff member an expected response time. The expected response time receiver 354 may be connected to the selector (not shown); for example, to allow the selector to select an alternative staff member in case the selected staff member is unresponsive or unable to respond in time. The expected response time receiver 354 may be combined with the alert signal sender 340; for example, both may need to interface with the same mobile telecommunication network.

Router 160 may also comprise a display sender 350 and a display location database 352. Display sender 350 selects a display that is near, say nearest, to the origin of the alert. For example, display sender 350 selects from a list of displays and associated locations stored in database 352 the nearest one to the location of the alert generation device, e.g., the location at the time the alert was received by router 160. Display sender 350 may then send a message to the selected display. The selected display is close to the alert generation device so it is likely that the message can be read by the patient concerned in the alert. The message for display on the selected display may comprise the expected response time.

The database may also list for each alert location a display to use. In this way a lot of flexibility is achieved to make sure the displays may be read from the alert location. It is also possible to combine these approaches, for example a set of displays may be assigned to an area, say a room. When an alert originates from that area, the nearest display in that area is used to display the message.

For example, if device 122 generates an alert, the router 160 may determine that staff member 151 is unavailable. If both members 152 and 153 are suitable, then member 152 may be selected since it is closer to the alert than member 153. A message may be shown on display 131. If member 152 responded with an expected response time, the expected response time may be shown on display 131.

For example, if device 124 generates an alert, the router may determine that member 152 and 153 may both respond. Even though other members may be closer, the router may select member 153 since he is in the same room.

Alert generation device 125 may be a mobile fall detector. If it detects a fall, the router may direct member 152, being the nearest. The router may also or instead send an alert to member 153 if he is more suitable for fall accidents. Display 134 may show a message that the fall has been detected. Router 160 may send a message to multiple displays in the area from which an alert originated, e.g., also a message may be sent to display 133.

Typically, router, localization devices, alert generation devices and individually addressable mobile device each comprise a microprocessor (not shown) which executes appropriate software stored at the respective device, e.g. that the software may have been downloaded and stored in a corresponding memory, e.g. RAM (not shown). The devices router, localization devices, alert generation devices and individually addressable mobile device may also be equipped with antenna's (not shown) to allow wireless communication.

Part of router, localization devices, alert generation devices and individually addressable mobile device may be embodied as dedicated hardware, e.g., in the form of silicon gates.

Many different ways of executing the methods are possible, as will be apparent to a person skilled in the art. For example, the order of the steps can be varied or some steps may be executed in parallel. Moreover, in between steps other method steps may be inserted. The inserted steps may represent refinements of the method such as described herein, or may be unrelated to the method. For example, steps 410 and 420 may be executed, at least partially, in parallel. Moreover, a given step may not have finished completely before a next step is started.

A method according to the invention may be executed using software, which comprises instructions for causing a processor system to perform method 400. Software may only include those steps taken by a particular sub-entity of the system. The software may be stored in a suitable storage medium, such as a hard disk, a floppy, a memory etc. The software may be sent as a signal along a wire, or wireless, or using a data network, e.g., the Internet. The software may be made available for download and/or for remote usage on a server.

It will be appreciated that the invention also extends to computer programs, particularly computer programs on or in a carrier, adapted for putting the invention into practice. The program may be in the form of source code, object code, a code intermediate source and object code such as partially compiled form, or in any other form suitable for use in the implementation of the method according to the invention. An embodiment relating to a computer program product comprises computer executable instructions corresponding to each of the processing steps of at least one of the methods set forth. These instructions may be subdivided into sub-routines and/or be stored in one or more files that may be linked statically or dynamically. Another embodiment relating to a computer program product comprises computer executable instructions corresponding to each of the means of at least one of the systems and/or products set forth.

It should be noted that the above-mentioned embodiments illustrate rather than limit the invention, and that those skilled in the art will be able to design many alternative embodiments.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A method for routing a medical alert to a selected staff member in a hospital, the method comprising
   receiving first alert signal generated by an alert generation device carried by, connected to, or in the vicinity of a patient,
   obtaining the current location and identity of multiple staff members from a location tracking system configured to track the locations of the multiple staff members,
   upon receiving the first alert signal,
   determining which staff members of the multiple staff members are available to respond to the alert, including determining that a current location of a particular staff member matches a room within the hospital designated in a database as unavailable, and classifying the particular staff member as unavailable in response to the determination that the current location matches the room designated in the database as unavailable,
   selecting from the multiple suitable staff members a selected staff member that is available to respond to the alert type and by at least determining that the distance between the location of the alert generation device and the location of the selected staff member is shorter than the distance between the location of the alert generation device and the location of at least one of the multiple suitable staff members other than the selected staff member that is also available to respond,
   sending a second alert signal to an individually addressable mobile device associated with the selected staff member;
   selecting, from a list of multiple output devices and associated locations stored in the database or a different database, a selected output device closest to the location of the alert generation device; and
   sending a message to the selected output device for rendition to the patient.

2. The method of claim 1, wherein the selected output device comprises a display.

3. The method of claim 1, wherein the selected output device comprises a speaker.

4. The method of claim 1, wherein the alert generation device is a mobile alert generation device, the method further comprising
   obtaining the current location of the mobile alert generation device from a location tracking system configured to track the location of the mobile alert generation device.

5. The method of claim 4, wherein the mobile alert generation device comprises a fall detector, the mobile alert generation device being configured to generate the alert upon the fall detector detecting the fall of a person carrying the mobile alert generation device.

6. The method of claim 4, further comprising
   detecting that the location of the mobile alert generation device remains in an alert area for a period exceeding an alert period.

7. The method of claim 1, further comprising
   receiving from the selected staff member an expected response time, and wherein the message for rendition to the patient on the selected output device comprises the expected response time.

8. An alert router for routing a medical alert to a selected staff member in a hospital, the alert router comprising
   a receiver configured to receive a first alert signal generated by an alert generation device carried by, connected to, or in the vicinity of a patient,
   a location obtainer configured to obtain the current location and identity of multiple staff members from a location tracking system configured to track the locations of the multiple staff members,
   a selector configured to upon receiving the first alert signal,
   determine which staff members of the multiple staff members are available to respond to the alert, a particular staff member is determined as unavailable if its location is in a defined unavailability room within the hospital,
   select from the multiple suitable staff members a selected staff member that is available to respond to the alert type and by at least determining that the distance between a location of the alert generation device and the location of the selected staff member is shorter than the distance between the location of the alert generation device and the location of at least one of the multiple suitable staff members other than the selected staff member that is also available to respond,
   an alert signal sender configured to:

send a second alert signal to an individually addressable mobile device associated with the selected staff member;

select, from a list of multiple displays and associated locations stored in a database, a selected display closest to the location of the alert generation device; and sending a message to the selected display for display to the patient.

9. A non-transitory computer-readable medium comprising instructions that cause a computing system to perform all the steps of claim 1 when the instructions are executed by the computing system.

10. The alert router of claim 8, wherein determining that a particular staff member is unavailable if its location is in a defined unavailability room of the hospital includes determining that a current location of the particular staff member matches the defined unavailability room, and classifying the particular staff member as busy in response to the determination that the current location matches the defined unavailability room.

11. A non-transitory computer-readable medium comprising instructions that, in response to execution of the instructions by a computing system, cause the computing system to:

detect that a location of a mobile alert generation device carried by a patient remains in an alert room of a hospital for a period exceeding an alert period, wherein the alert room is associated in a database with the alert period;

raise a first alert signal in response to the detecting;

obtain the current location and identity of multiple staff members from a location tracking system configured to track the locations of the multiple staff members;

upon receipt of the first alert signal;

determine that one or more current locations of one or more particular staff members match one or more rooms designated in a database as unavailable;

classify the one or more particular staff members as unavailable in response to the determination that the one or more current locations of the one or more particular staff members match one or more rooms designated in the database as unavailable;

select from multiple suitable staff members a selected staff member that is available to respond to the alert type and by at least determining that the distance between a location of the alert generation device and the location of the selected staff member is shorter than the distance between the location of the alert generation device and the location of at least one of the multiple suitable staff members other than the selected staff member that is also available to respond; and send a second alert signal to an individually addressable mobile device associated with the selected staff member.

12. The non-transitory computer-readable medium of claim 11, further comprising instructions that, in response to execution of the instructions by the computing system, further cause the computing system to:

select from multiple output devices a selected output device closest to the location of the alert generation device; and upon receipt of the first alert signal, send a message to the selected output device for rendition to the patient.

13. The non-transitory computer-readable medium of claim 12, wherein the selected output device comprises a display.

14. The non-transitory computer-readable medium of claim 12, wherein the selected output device comprises a speaker.

15. The non-transitory computer-readable medium of claim 12, further comprising instructions that, in response to execution of the instructions by the computing system, further cause the computing system to receive from the selected staff member an expected response time, and wherein the message for rendition to the patient on the selected output device comprises the expected response time.

* * * * *